United States Patent [19]

Farge et al.

[11] 4,154,598
[45] May 15, 1979

[54] HERBICIDAL 1,2,4-OXADIAZIN-5-ONE COMPOSITIONS

[75] Inventors: Daniel Farge, Thiais; Jean Leboul, Gif; Yves Le Goff, Bretigny; Gilbert Poiget, Thiais, all of France

[73] Assignee: Philagro, France

[21] Appl. No.: 874,624

[22] Filed: Feb. 2, 1978

Related U.S. Application Data

[63] Continuation of Ser. No. 722,165, Sep. 10, 1976, abandoned.

[30] Foreign Application Priority Data

Sep. 11, 1975 [FR] France .................. 75 27885

[51] Int. Cl.² .................. A01N 9/14; A01N 9/22; C07D 413/02
[52] U.S. Cl. .................. 71/90; 71/92; 544/66
[58] Field of Search .................. 71/90, 92; 544/66

[56] References Cited

U.S. PATENT DOCUMENTS 3,574,201  4/1971  Breuer .................. 544/66 X
3,600,386  8/1971  Levitt .................. 71/92
3,877,924  4/1975  Fischer .................. 71/92

OTHER PUBLICATIONS

Poignant, Chemical Abstracts, vol. 77, Abst. No. 148549w (1972), (abst. of Fr. Demande 2,097,085).

*Primary Examiner*—John D. Randolph
*Attorney, Agent, or Firm*—Robert E. Burns; Emmanuel J. Lobato; Bruce L. Adams

[57] ABSTRACT

Herbicidal and/or phyto-hormonal compositions containing 1,2,4-oxadiazin-5-one of the formula

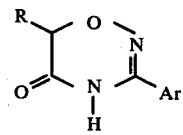

where R represents H, alkyl or phenyl and Ar represents substituted phenyl or a 5 membered aromatic heterocyclic radical with O, S or N as the hetero-atom and optionally substituted are described.

10 Claims, No Drawings

HERBICIDAL 1,2,4-OXADIAZIN-5-ONE COMPOSITIONS

This is a continuation of application, Ser. No. 722,165, filed Sept. 10, 1976 and now abandoned.

THE INVENTION

The present invention relates to new 1,2,4-oxadiazin-5-one derivatives of the formula:

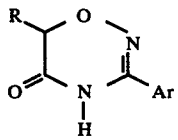
(I)

their preparation, the compositions in which they are present and the agricultural treatments carried out by means of these compositions.

In the general formula (I),

R represents a hydrogen atom or an alkyl radical containing 1 to 4 carbon atoms or a phenyl radical, and Ar represents a phenyl radical substituted by 1 to 3 identical or different substituents chosen from amongst halogen atoms and the following radicals: alkyl containing 1 to 4 carbon atoms, hydroxyl, alkoxy of which the alkyl part contains 1 to 4 carbon atoms, alkylthio of which the alkyl part contains 1 to 4 carbon atoms, alkylsulphinyl of which the alkyl part contains 1 to 4 carbon atoms, alkylsulphinyl of which the alkyl part contains 1 to 4 carbon atoms, alkyisulphonyl of which the alkyl part contains 1 to 4 carbon atoms, trifluoromethyl, trifluoromethoxy, trifluoromethylthio, carboxyl, alkoxycarbonyl of which the alkyl part contains 1 to 4 carbon atoms, nitro, amino, alkylamino of which the alkyl part contains 1 to 4 carbon atoms, dialkylamino of which each alkyl part contains 1 to 4 carbon atoms, acylamino of which the acyl part contains 1 to 4 carbon atoms, alkoxycarbonylamino of which the alkyl part contains 1 to 4 carbon atoms, azido, alkanoyl containing 1 to 4 carbon atoms, sulphamoyl, dialkylsulphamoyl of which each alkyl part contains 1 to 4 carbon atoms, or phenyl, or Ar represents an aromatic heterocyclic radical with 5 chain members which contains an atom of oxygen, of sulphur or of nitrogen as the hetero-atom and is optionally substituted by an atom or radical chosen from amongst the halogen atoms and the following radicals: alkyl containing 1 to 4 carbon atoms, phenylalkyl of which the alkyl part contains 1 to 4 carbon atoms, alkoxy of which the alkyl part contains 1 to 4 carbon atoms or alkylthio of which the alkyl part contains 1 to 4 carbon atoms.*

*Footnote: The chemical term "radical" is used as interchangeable with the term "group". Either usage is to be understood and acceptable.

According to the invention, the new products of the general formula (I) can be prepared by cyclizing a product of the general formula

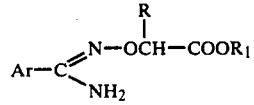
(II)

Process A in which Ar and R are defined as above and $R_1$ represents an alkyl radical containing 1 to 4 carbon atoms.

In general, the cyclization is carried out by heating in a basic medium. It is particularly advantageous to work in an organic solvent such as pyridine or in an alcohol such as ethanol, in the presence of an alkali metal alcoholate such as sodium methylate or sodium ethylate.

The products of the general formula (II) can be obtained in accordance with one of the following methods:

1. By the action of an α-halogen-ester of the general formula:

$$Y-\underset{R}{\underset{|}{CH}}-COOR_1 \quad \text{(III)}$$

in which R and $R_1$ are defined as above and Y represents a halogen atom, on an amidoxime of the general formula:

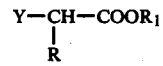
(IV)

in which Ar is defined as above.

The reaction is generally carried out in an aqueous organic solvent such as a mixture of ethanol and water or of dimethylformamide and water in the presence of an alkaline condensation agent such as sodium hydroxide and at a temperature of between 20° and 80° C. In certain cases, this reaction makes it possible to obtain the cyclized compound (I) directly without going through the intermediate compound II.

The products of the general formula (IV) can be obtained by the action of hydroxylamine on a nitrile of the general formula:

$$Ar-CN \quad \text{(V)}$$

in which Ar is defined as above.

In general, the reaction is carried out in an organic solvent such as aqueous ethanol at a temperature of between 20° and 80° C.

2. By the action of an α-aminoxy-ester of the general formula:

$$H_2N-O-\underset{R}{\underset{|}{CH}}-COOR_1 \quad \text{(IV)}$$

in which R and $R_1$ are defined as above, on an imino-ether salt of the general formula:

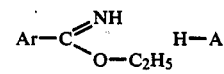
(VII)

in which Ar is defined as above and HA represents a molecule of hydrochloric acid (HCl) or of fluoboric acid ($HBF_4$).

In general, the reaction takes place in a basic organic solvent such as pyridine at a temperature of about 20° C.

The imino-ether salt of the general formula (VII) can be obtained by the action of a solution of hydrogen chloride in ethanol on a nitrile of the general formula (V) or by the action of triethyloxonium fluoborate (Merwin salt) or an amide of the general formula:

$$Ar-CONH_2 \quad \text{(VIII)}$$

in which Ar is defined as above.

3. By the action of a compound of the formula:

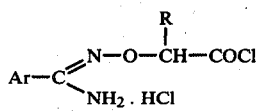

on a compound of the formula $R_1OH$ (X), Ar, R and $R_1$ being defined as above. The reaction is carried out by heating the compound (IX) in the presence of the alcohol (X).

According to the invention, the new products of the general formula (I) can also be obtained by the action of an α-aminoxy-ester of the general formula (VI) on an imino-ether salt of the general formula (VII), in a basic organic solvent such as pyridine at the reflux temperature (Process B).

According to the invention, the new products of the general formula (I) can also be obtained by treating a product of the general formula:

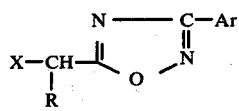

in which R and Ar are defined as above and X represents a halogen atom, preferably a chlorine or bromine atom, with an alkali metal hydroxide in aqueous solution (Process C).

The products of the general formula (XI) can be obtained by the action of an acid chloride of the general formula:

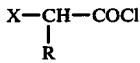

in which R and X are defined as above, on an amidoxime of the general formula (IV).

In general, the reaction is carried out in an organic solvent such as dioxane and toluene in the presence of pyridine.

The new products of the general formula (I) can optionally be purified by physico-chemical methods such as crystallization or chromatography.

METHODS AND COMPOSITIONS FOR USE

The products according to the present invention exhibit remarkable properties which render them particularly useful in the agricultural field.

If they are used at doses of between 1 and 100 g/hl of water, they exhibit particularly valuable phytohormonal properties. In that case, they possess auxinic actions analogous to those of indolylacetic acid or of derivatives of the phenoxyacetic acids. They are essentially useful in assisting the setting of fruit on certain plants (tomatoes), preventing the shedding of leaves or fruit or increasing the formation of roots.

If they are used at doses of between 0.5 and 10 kg/ha, the products according to the invention exhibit herbicidal properties, in particular against dicotyledon plants, both in pre-emergence and in post-emergence.

The present invention also relates to the compositions for agricultural use which contain, as the active product, at least one derivative of the general formula (I) in association with a carrier and/or a surface-active agent and optionally one or more adjuvants which are compatible with the active product or products and can be used in agriculture. These compounds can contain other compatible pesticides such as fungicides or insecticides. In these compositions the content of active product can be between 0.005 and 95% by weight.

The term "carrier" in the sense of the present description denotes an organic or inorganic, natural or synthetic material, with which the active material is associated in order to facilitate its application to the plant, to the seed or to the soil, or its transport, or its handling. The carrier can be solid (clays, natural or synthetic silicates, resins, waxes, solid fertilizers and the like) or fluid (water, alcohols, ketones, petroleum fractions, chlorinated hydrocarbons or liquified gases).

The surface-active agent can be an emulsifier, a dispersing agent or wetting agent and each of these can be ionic or nonionic. By way of example there may be mentioned the salts of polyacrylic acids and of ligninsulphonic acids, and condensate of ethylene oxide with fatty alcohols, fatty acids or fatty amines.

The compositions according to the invention can be prepared in the form of wettable powders, dusting powders, granules, solutions, emulsifiable concentrates, emulsions, suspension concentrates and aerosols.

The wettable powders are usually prepared in such a way that they contain from 20 to 95% by weight of active material, and they usually contain, in addition to a solid carrier, from 0 to 5% of wetting agent, from 3 to 10% by weight of a dispersing agent and, where necessary, from 0 to 10% by weight of one or more stabilizers and/or other additives, such as penetrating agents, adhesives or anti-caking agents, dyestuffs and the like.

The powders for dusting are usually prepared in the form of a dust concentrate having a composition similar to that of a wettable powder, but without dispersing agent, and are diluted, at the use site, with a supplementary amount of a solid carrier so that a composition which usually contains from 0.5 to 10% by weight of active material is obtained.

The emulsifiable concentrates which can be applied by spraying usually contain, in addition to the solvent and, where necessary, a co-solvent, from 10 to 50% by weight/volume of active material, from 2 to 20% by weight/volume of emulsifiers and from 0 to 20% by weight/volume of appropriate additives, such as stabilizers, penetrating agents, corrosion inhibitors, dyestuffs and adhesives.

The suspension concentrates, which can also be applied by spraying, are prepared so that a stable fluid product which does not sediment is obtained, and they usually contain from 10 to 75% by weight of active material, from 0.5 to 15% by weight of surface-active agents, from 0.1 to 10% by weight of antisedimentation agents such as protective colloids and thixotropic agents, from 0 to 10% by weight of appropriate additives, such as anti-foam agents, corrosion inhibitors, stabilizers, penetrating agents and adhesives and, as the carrier, water or an organic liquid in which the active material is substantially insoluble; certain organic solid materials or inorganic salts can be dissolved in the carrier to assist in preventing the sedimentation or to act as antifreeze agents for the water.

Aqueous dispersions and emulsions, for example compositions obtained by diluting a wettable powder or an emulsifiable concentrate according to the invention with water, also fall within the general scope of the present invention. These emulsions can be of the water-in-oil type or of the oil-in-water type and can have a thick consistency such as that of a "mayonnaise".

For a so-called "ultra-low volume" application, entailing spraying as very fine droplets, solutions, in organic solvents, which contain from 70 to 99% of active material are prepared.

The compositions according to the invention can contain other ingredients, for example protective colloids, adhesive or thickeners, thixotropic agents, stabilizers or sequestering agents as well as other known active materials having pesticidal properties, in particular insecticides or fungicides.

By way of example, the composition of a wettable powder is given below, the percentages being expressed by weight:

Active material—50%
Calcium lignosulphate (deflocculating agent)—5%
Isopropylnaphthalenesulphonate (wetting agent)—1%
Silica anti-caking agent—5%
Filler (kaolin)—39%

The examples which follow and are given, without implying a limitation, show how the invention may be put into practice.

DETAILED DESCRIPTION

EXAMPLE 1: PROCESS B

Ethyl 4-chloro-benzimidate hydrochloride (47.8 g.), ethyl amino-oxyacetate hydrochloride (34 g.) and anhydrous pyridine (820 cc.) are kept at the boil, while stirring, for 16 hours. The pyridine is evaporated under reduced pressure (20 mm Hg) and concentrate is then taken up with ethyl acetate (600 cc.) and water (300 cc.).

The organic phase is decanted and then washed with water (3×100 cc.)

After drying over anhydrous sodium sulphate, the solvent is evaporated under reduced pressure (20 mm Hg). The solid residue is taken up in isopropyl ether (100 cc.) and the crystals are filtered off.

3-(4-Chlorophenyl)-5,6-dihydro-4H-1,2,4-oxadiazin-5-one (24.1 g.) is thus obtained.

After recrystallization from ethanol (7 parts by volume), the product melts at 170° C.

Ethyl 4-chloro-benzimidate hydrochloride, used as the starting material, can be prepared by the method of L. WEINTRAUB, S. R. OLES and N. KALISH, J. Org. Chem. 33, 7,679 (1963).

EXAMPLE 2

Following the procedure of Example 1, but starting from ethyl 2-chloro-benzimidate hydrochloride and ethyl aminoxyacetate hydrochloride, 3-(2-chlorophenyl)-5,6-dihydro-4H-1,2,4-oxadiazin-5-one, melting at 132° C., is obtained in a yield of 80%.

EXAMPLES 3 TO 6

Following the procedure of Example 1, and starting from suitable starting materials, the following products are obtained:

| Ex. No. | Ar | R | Yield | Melting point, °C. after recrystallization |
|---|---|---|---|---|
| 3 | -C6H4-OH | H | 66% | 251 |
| 4 | -C6H4-OCH3 | H | 63% | 212 |
| 5 | -C6H3(Cl)(Cl) | H | 58% | 179 |
| 6 | -C6H4-SCH3 | H | 67% | 128 |

EXAMPLE 7: PROCESS A

O-Ethoxycarbonylmethyl-5-chlorothiophene-2-carboxamidoxime (14.1 g.) and dry sodium methylate (2.9 g.) in ethanol (140 cc.) are stirring at ambient temperature for 3 hours. The ethanol is evaporated under reduced pressure and the solid residue is then taken up in distilled water (100 cc.).

The solution thus obtained is acidified by adding N hydrochloric acid (54 cc.). The white crystals formed are filtered off and washed with water.

After drying, 3-(5-chlorothienyl-2)-5,6-dihydro-4H-1,2,4-oxadiazin-5-one (10.7 g.), melting at 210° C., is obtained.

EXAMPLES 8 TO 31

Following the procedure of Example 7, starting from suitable starting materials, the following products are obtained:

| Ex. No. | Ar | R | Yield | Melting point °C. after recrystallization |
|---|---|---|---|---|
| 8 | thienyl (S) | H | 72% | 180 |
| 9 | thienyl (S) | —CH3 | 87% | 187 |
| 10 | thienyl (S) | H | 96% | 183 |
| 11 | furyl (O) | H | 77% | 186 |
| 12 | thienyl-Cl (S) | H | 90% | 210 |
| 13 | thienyl-CH3 (S) | H | 92% | 215 |
| 14 | N-CH3 pyrrolyl | H | 69% | 143 |

-continued

| Ex. No. | Ar | R | Yield | Melting point °C. after recrystallization |
|---|---|---|---|---|
| 15 | N-methylpyrrole (2-yl) | H | 91% | 261 |
| 16 | 2-methylthien-5-yl | H | 89% | 100 |
| 17 | 2-bromothien-5-yl | H | 89% | 127 |
| 18 | 4-N(CH₃)₂-phenyl | H | 81% | 210 |
| 19 | 4-NO₂-phenyl | H | 90% | 210 |
| 20 | 4-I-phenyl | H | 84% | 146 |
| 21 | 4-OH-phenyl | H | 73% | 184 |
| 22 | 3-Cl-phenyl | H | 81% | 130 |
| 23 | 3-NO₂-4-Cl-phenyl | H | 68% | 203 |
| 24 | 4-F-phenyl | H | 76% | 148 |
| 25 | 2-F-phenyl | H | 71% | 126 |
| 26 | 4-SO₂N(CH₃)₂-phenyl | H | 81% | 190 |
| 27 | 3-SO₂N(CH₃)₂-phenyl | H | 93% | 164 |
| 28 | 3-SO₂NH₂-phenyl | H | 64% | 204 |
| 29 | 3-SCF₃-phenyl | H | 76% | 132 |
| 30 | 3-SO₂CH₃-phenyl | H | 97% | 203 |
| 31 | 2-Br-phenyl | H | 77% | 123 |

EXAMPLE 32

This example describes the preparation of 3-(thienyl-2)-5,6-dihydro-4H-1,2,4-oxadiazin-5-one by means of Process C.

This same compound has already been described in Example 8, the process of preparation used there being Process A.

Chloroacetyl chloride (1.13 g.) is added dropwise, over the course of 10 minutes, to a solution of thiophene-2-carboxamidoxime (1.42 g.) in dioxane (20 cc.). The white precipitate obtained is dissolved by adding pyridine (3 cc.) to the reaction mixture. After 16 hours at a temperature of about 20° C., a brown oil separates out. The solvents are evaporated at a temperature of about 20° C. under reduced pressure (40 mm Hg followed by 1 mm Hg), and the concentrate is then taken up in water (10 cc.). The precipitate obtained is filtered off and washed with water (2×5 cc.). After drying, O-chloroacetyl-thiophene-2-carboxamidoxime (1.1 g.) melting at 156° C. is obtained.

O-chloroacetyl-thiophene-2-carboxamidoxime (1 g.) is dissolved in toluene (20 cc.) and the solution is heated under reflux for 16 hours. After decolorizing with animal charcoal, the solution is concentrated under reduced pressure (20 mm Hg) and the crystals which deposit are dried under reduced pressure (1 mm Hg) at a temperature of about 20° C. 5-chloromethyl-3-(thienyl-2)-1,2,4-oxadiazole (0.9 g.) melting at 57° C. is thus obtained.

5-chloromethyl-3-(thienyl-2)-1,2,4-oxadiazole (0.67 g.) is dissolved in dimethylformamide (5 cc.). A 2 N aqueous sodium hydroxide solution (5 cc.) is added to the solution obtained and the mixture is stirring for 30 minutes. It is acidified with 11 N hydrochloric acid (0.9 cc.) and the crystals obtained are filtered off and washed with water (4×10 cc.).

After drying, 3-(thienyl-2)-5,6-dihydro-4H-1,2,4-oxadiazin-5-one (0.46 g.) melting at 180° C. is obtained.

EXAMPLE 33

The compound described in this example was prepared in accordance with a variant of Process A, by directly reacting an α-halogeno-ester of the general formula (III) with an amidoxime of the general formula (IV). In this case, the intermediate product (II) was not identified and reaction of the compound (III) with the compound (IV), and cyclization of the resulting product, took place simultaneously.

Thiophene-2-carboxamidoxime (28.4 g.) is added to a 2 N ethanolic sodium hydroxide solution (200 cc.), and a solution of ethyl bromobutyrate in ethanol (200 cc.) is then added over the course of 30 minutes. The reaction mixture is stirring for 16 hours and the alcohol is then distilled at a temperature of about 25° C. under reduced pressure (20 mm Hg). The residue obtained is taken up in water (200 cc.) and ether (100 cc.). The organic phase is decanted and washed with water (100 cc.). The aqueous liquors are combined and acidified with citric acid (14 g.). A precipitate is obtained, which is filtered off and washed with water (3×20 cc.) and then dried at a temperature of about 20° C. under reduced pressure (1 mm Hg). 6-ethyl-3-(thienyl-2)-5,6-dihydro-4H-1,2,4-oxadiazin-5-one (10.38 g.), melting at 171° C., is thus obtained.

After recrystallization from acetonitrile, the pure product melts at 176° C.

EXAMPLE 34

On following the procedure of Example 33, starting from thiophene-2-carboxamidoxime (20 g.) and ethyl α-bromophenylacetate (34.2 g.), 6-phenyl-3-(thienyl-2)-5,6-dihydro-4H-1,2,4-oxadiazin-5-one (10.3 g.); melting at 173° C. after recrystallization, is obtained.

EXAMPLE 35

A condensation product (10 parts) of ethylene oxide and octylphenol in the ratio of 10 molecules of ethylene oxide per molecule of octylphenol is added to a solution of 3-(thienyl-2)-5, 6-dihydro-1,2,4-oxadiazin-5-one (25 parts) in a mixture (65 parts) of equal parts of toluene and acetophenone. The solution is used after dilution with water at the rate of 100 cc. of this solution per 100 liters of water.

The phytohormonal activity of the products of the present application can be demonstrated in the following tests:

(1) SETTING OF FRUIT OF TOMATOES 1 drop (0.05 cc) of the solution or suspension of the product to be studied is deposited on the ovary of emasculated flowers of tomato plants. After a period of observation of 15 days, the percentage of fruit formed relative to the comparison is noted.

Used in this way, at a concentration of 100 mg./liter, the product of Example 8 shows a degree of setting of fruit of 100%, relative to the comparison (0%). The fruit formed is devoid of pips.

(2) PROPAGATION BY CUTTINGS OF TOMATO LEAVES

The 3rd and 4th leaves are taken from tomato stems (Marmande variety) having 5 to 6 leaves. The petiole of each leaf is dipped, over a length of 2 to 3 cm, into the solution to be studied, contained in a test tube. 8 days after starting the experiment, the number of roots formed on the petioles of the treated leaves is counted and measured.

Used in this way, at a concentration of 10 mg./liter, the product of Example 8 causes the formation of 100% of rooted leaves, while the formation is zero in the case of the petioles of the comparison plants.

In the same way, but at a concentration of 1 mg/liter, the products of examples 9 and 11 cause the formation of 100% of rooted leaves. With product of example 9, the roots are short and thick; with product of example 11, the roots are short and thin.

The herbicidal activity of the products of the general formula (I) can be demonstrated in the following manner:

Seeds of various species, namely wheat: *Triticum sativum*, lentil: *Lens culinaris*, radish: *Raphanus sativus*, sugar beet: *Beta vulgaris* and slender foxtail: *Alopecurus agrestis* are sown in plastic pots (180 cc. capacity), containing, to a height of 6 cm, a mixture composed of ⅓ of clean earth, ⅓ of vegetable mould and ⅓ of river sand, at the rate of about 30 seeds per pot. For each concentration of product, 2 pots of wheat and four pots of the other species are used.

For the purpose of a post-emergence treatment, the sowing is carried out in a greenhouse one week before the start of the experiment, so that the small plants are at the following stage at the time of treatment:

wheat and foxtail: 2 to 3 leaves lentil: 3 true leaves beet and radish: 2 well-developed cotyledon leaves.

The treatment is carried out by spraying the solution or suspension of the product, the pots being placed on a pot-turner. Each pot is given 1 cc. of the solution. The doses of the product to be studied are 1 and 8 kg/ha.

In pre-emergence, the seeded surface of the pots is allowed to dry and is then covered to a height of 1 cm with the same soil mixture. The pots are watered by spraying twice daily.

In post-emergence testing, the treated small plants are allowed to dry. The earth mixture is moistened by placing the base of the pots in a tray containing water.

In both cases, the pots are kept in a greenhouse (22° to 24° C., 70 to 80% relative humidity) under artificial light which provides 5,000 to 6,000 Lux at the level of the plants, for 17 consecutive hours per day.

Three weeks after the start of the treatment, the number of plants in each pot is counted, and their height is measured.

The results are expressed in percentages relative to the comparison plants. The results are summarized in the table which follows:

| Product of example | PRE EMERGENCE | | | | | | | | | | POST-EMERGENCE | | | | | | | | | |
|---|---|---|---|---|---|---|---|---|---|---|---|---|---|---|---|---|---|---|---|---|
| | Wheat | | Lentil | | Radish | | Beet | | Foxtail | | Wheat | | Lentil | | Radish | | Beet | | Foxtail | |
| kg/ha | 1 | 8 | 1 | 8 | 1 | 8 | 1 | 8 | 1 | 8 | 1 | 8 | 1 | 8 | 1 | 8 | 1 | 8 | 1 | 8 |
| 1 | 10 | 50 | 0 | 25 | 0 | 100 | 0 | 70 | 0 | 60 | 0 | 0 | 0 | 0 | 0 | 0 | 0 | 0 | 0 | 0 |
| 8 | 0 | 0 | 90 | 100 | 30 | 90 | 0 | 0 | 50 | 95 | 0 | 0 | 90 | 100 | 90 | 100 | 0 | 0 | 0 | 0 |
| 9 | 0 | 0 | 100 | 100 | 40 | 100 | 20 | 100 | 50 | 75 | 0 | 0 | 70 | 100 | 0 | 0 | 0 | 20 | 0 | 0 |
| 10 | 0 | 0 | 80 | 100 | 0 | 0 | 0 | 0 | 0 | 0 | 0 | 0 | 40 | 50 | 0 | 0 | 0 | 0 | 0 | 0 |

| Product of example | PRE EMERGENCE | | | | | | | | | | POST-EMERGENCE | | | | | | | | | |
|---|---|---|---|---|---|---|---|---|---|---|---|---|---|---|---|---|---|---|---|---|
| | Wheat | | Lentil | | Radish | | Beet | | Foxtail | | Wheat | | Lentil | | Radish | | Beet | | Foxtail | |
| 11 | 0 | 0 | 100 | 100 | 20 | 90 | 20 | 80 | 85 | 100 | 0 | 0 | 40 | 75 | 0 | 20 | 0 | 0 | 0 | 20 |
| kg/ha | 1 | 10 | 1 | 10 | 1 | 10 | 1 | 10 | 1 | 10 | 1 | 10 | 1 | 10 | 1 | 10 | 1 | 10 | 1 | 10 |
| Example | 0 | 10 | 60 | 100 | 25 | 100 | 0 | 50 | 40 | 60 | 0 | 20 | 30 | 100 | 0 | 60 | 0 | 20 | 0 | 20 |
| 15 | 0 | 20 | 100 | 100 | 0 | 100 | 50 | 50 | 50 | 85 | 30 | 60 | 50 | 100 | 0 | 40 | 0 | 20 | 0 | 20 |
| 16 | 0 | 0 | 60 | 100 | 0 | 0 | 0 | 50 | 50 | 60 | 0 | 0 | 0 | 90 | 0 | 40 | 0 | 50 | 0 | 0 |

What is claimed is:
1. A new derivative of 1,2,4-oxadiazin-5-one, of the formula:

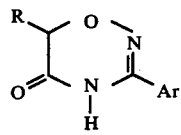

in which:
R represents a hydrogen atom, an alkyl radical containing 1 to 4 carbon atoms or a phenyl radical, and
Ar represents an aromatic heterocyclic radical with 5 members which contains an atom of oxygen, sulfur or nitrogen as the hetero-atom and is optionally substituted by a member selected from the group consisting of halogen, alkyl, phenylalkyl, alkoxy and alkylthio wherein each alkyl group contains 1 to 4 carbon atoms.

2. The compound according to claim 1, of the formula:

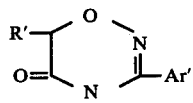

in which:
R' represents a hydrogen atom, a methyl radical or a phenyl radical and
Ar' represents a heteroaromatic radical with 5 members, which contains an oxygen, sulfur or nitrogen atom as the hetero-atom and is optionally substituted by a member selected from the group consisting of halogen and the methyl radical.

3. The compound according to claim 1 wherein Ar is a thienyl radical, optionally substituted by a member selected from the group consisting of halogen, alkyl, phenylalkyl, alkoxy, alkylthio wherein the alkyl portion of each group contains 1 to 4 carbon atoms and
R is hydrogen, alkyl of 1 to 4 carbon atoms or a phenyl radical.

4. A phytohormonal and herbicidal composition which contains a pytohormonal or herbicidal effective amount of at least one compound as defined in claim 1, in association with at least one agriculturally acceptable carrier and/or surface-active agent.

5. The composition according to claim 4, wherein the content of active material is between 0.005 and 95% by weight.

6. A process for phytohormonal or herbicidal the treatment of plants wherein a composition according to claim 4 is applied in a phytohormonal or herbicidal effective amount to the plants or their environs.

7. A compound of claim 1 wherein Ar is an unsubstituted aromatic heterocyclic radical with 5 members which contains oxygen, sulfur or nitrogen as the hetero-atom.

8. A compound of claim 1 which is 3-(thienyl-2)-5,6-dihydro-4H-1,2,4-oxadiazin-5-one.

9. A compound of claim 1 which is 3-(thienyl)-2)-6-methyl-5,6-dihydro-4H-1,2,4-oxadiazin-5-one.

10. A compound of claim 1 which is 3-(thienyl-3)-5,6-dihydro-4H-1,2,4-oxadiazin-5-one.

* * * * *